United States Patent [19]
Tsuijino

[11] Patent Number: 5,403,357
[45] Date of Patent: Apr. 4, 1995

[54] HAIR COLORING COMPOSITION CONTAINING STEARATE DERIVATIVES AS DRYING INHIBITORS

[75] Inventor: Yoshio Tsujino, Izumisano, Japan
[73] Assignee: Yamahatsu Sangyo Kaisha, Ltd., Osaka, Japan
[21] Appl. No.: 955,874
[22] PCT Filed: Apr. 17, 1991
[86] PCT No.: PCT/JP91/00509
§ 371 Date: Dec. 11, 1992
§ 102(e) Date: Dec. 11, 1992
[87] PCT Pub. No.: WO92/18094
PCT Pub. Date: Oct. 29, 1992
[51] Int. Cl.⁶ ............................................. A61K 7/13
[52] U.S. Cl. ................................... 8/435; 8/405; 8/550
[58] Field of Search ............... 8/405, 406, 435, 550; 424/70

[56] References Cited

U.S. PATENT DOCUMENTS

| | | | |
|---|---|---|---|
| 3,661,500 | 5/1972 | Dehn, Jr. et al. | 8/10 |
| 4,088,751 | 5/1978 | Kenkare et al. | 424/47 |
| 4,725,282 | 2/1988 | Hoch et al. | 8/408 |
| 4,933,177 | 6/1990 | Grollier et al. | 424/74 |
| 5,064,441 | 11/1991 | Kawase et al. | 8/405 |
| 5,078,750 | 1/1992 | Komai et al. | 8/405 |
| 5,190,915 | 3/1993 | Behan et al. | 512/2 |
| 5,198,210 | 5/1993 | Critchley et al. | 424/78.03 |

FOREIGN PATENT DOCUMENTS

| | | |
|---|---|---|
| 6121448 | 1/1966 | Japan . |
| 1093515 | 4/1989 | Japan . |
| 1165513 | 6/1989 | Japan . |
| 1242518 | 9/1989 | Japan . |

OTHER PUBLICATIONS

McCutcheon's Emulsifiers & Detergents, North American Edition 1982 McCutcheon Division, MC Publishing Co., Glen Rock, N.J. USA p. 279.

*Primary Examiner*—Paul Lieberman
*Assistant Examiner*—Caroline L. Disheck
*Attorney, Agent, or Firm*—Adduci, Mastriani, Schaumbert & Schill

[57] ABSTRACT

A hair coloring composition comprising a coloring matter, a binder resin and an organic solvent, characterized in that the composition further contains an effective amount of at least one drying inhibitor selected from the group consisting of: a glyceryl stearate, a polyglyceryl stearate, a sorbitan stearate, a polyoxyethylene sorbitan stearate, a polyoxyethylene sorbitol stearate, a polyoxyethylene glyceryl stearate, and a propylene glycol stearate.

9 Claims, 2 Drawing Sheets

HAIR COLORING COMPOSITION CONTAINING STEARATE DERIVATIVES AS DRYING INHIBITORS

FIELD OF THE INVENTION

The present invention relates to a hair coloring composition.

BACKGROUND ART

Conventionally the application of a hair colorant to hair or the like necessitated dipping a brush or like applicator into the hair colorant held in a container and withdrawing the moistened applicator from the container. Thus, the application of hair colorants raised problems. For example, the application was very cumbersome and the hair colorant adhered to or soiled the container exterior or scattered because the periphery of applicator was unavoidably contacted with the mouth end of the container in withdrawal from the container.

Recently a new applicator was introduced in an attempt to facilitate application. The new applicator includes a hair colorant container having a valve means therein and a brush or the like on top, and is adapted to supply the hair colorant to its top by knocking to open a valve passage. The new applicator involves knocking and may supply an excessive colorant to the top by too much knocking in which case the colorant is likely to fall in drops or to scatter.

More recently, a new device of the wick-sucking type has been proposed to obviate the above problems (Japanese Unexamined Utility Model Publications 154830/1989 and 154831/1989). The device has a wick means formed of a bundle of fibers provided at a container top. One end of the wick means is dipped in a hair colorant within the container to bring the colorant to the other end of wick means protruded outside (application point) through the wick means due to the capillary action of fibers. The device of the wick-sucking type facilitates application and can effectively prevent the scatter of hair colorant from the application point but poses new problems. Since conventional hair colorants contain a volatile solvent and dry quickly, the device encounters the following problems. If the device is left to stand with its cap removed and with the wick means exposed to air at the application point, the so-called dry-up phenomenon occurs in which the other components such as a coloring matter and a resin are dried and solidified by the evaporation of a solvent from the colorant. This phenomenon blocks the flow of colorant at the application point, whereby a coating with a thin spot is formed or a supply of colorant is made impossible.

To overcome the above problems, a hair colorant of low vapor pressure and a slow-drying solvent may be used. This attempt, however, is not successful because the hair colorant impairs the drying property of coating and has an increased viscosity. The addition of a drying inhibitor may be considered but an effective drying inhibitor has not been proposed so far.

DISCLOSURE OF THE INVENTION

It is an object of the present invention to provide a hair coloring composition which would not change the formulation, namely would not deteriorate properties, on exposure to air for a prolonged period of time.

It is another object of the invention to provide a drying inhibitor for a hair colorant which inhibitor can effectively inhibit drying even at a small amount and therefore does not adversely affect the dispersion stability of pigment inherently possessed by the hair colorant nor the good feel of a coating attributable to the colorant.

It is a further object of the invention to provide a hair coloring composition which is able to effectively inhibit drying and solidifying at the application point in a container of the fiber bundle wick-sucking type without impairing the drying property of coating nor increasing the viscosity.

According to the present invention, there is provided a hair coloring composition comprising a coloring matter, a binder resin and an organic solvent, characterized in that the composition further contains an effective amount of at least one drying inhibitor selected from the group consisting of:

(a) a glyceryl stearate represented by the formula wherein $R_1$ and $R_2$ are the same or different and each represents a hydrogen atom or a stearoyl group, provided that $R_1$ and $R_2$ can not be a hydrogen atom at the same time;

(b) a polyglyceryl stearate represented by the formula wherein $R_1$, $R_2$, $R_3$, $R_4$, and $R_5$ are the same or different and each represents a hydrogen atom or a stearoyl group, provided that $R_1$, $R_2$, $R_3$, $R_4$, and $R_5$ can not be a hydrogen atom at the same time, and a is an integer of 0 or 1 to 13;

(c) a sorbitan stearate represented by the formula wherein $R_1$, $R_2$, and $R_3$ are as defined above, provided that $R_1$, $R_2$, and $R_3$ can not be a hydrogen atom at the same time;

(d) a polyoxyethylene sorbitan stearate represented by the formula wherein $R_6$ and $R_7$ are each a stearoyl group or $-(CH_2CH_2O)_cH$, b and c are each an integer of 0 or 1 to 10, $b+2c$ is an integer of 1 to 10, $R_8$ is a hydrogen atom or a stearoyl group, provided that when one or both of $R_6$ and $R_7$ are a stearoyl group, $R_8$ may be a hydrogen atom, but when both of $R_6$ and $R_7$ are $-(CH_2CH_2O)_cH$, $R_8$ is a stearoyl group;

(e) a polyoxyethylene sorbitol stearate represented by the formula $$\begin{array}{l} CH_2-O-(CH_2CH_2O)_b-R_1 \\ [CH-O-(CH_2CH_2O)_c-R_2]_4 \\ CH_2-O-(CH_2CH_2O)_d-R_3 \end{array} \quad (V)$$

wherein $R_1$, $R_2$, and $R_3$ are as defined above, provided that $R_1$, $R_2$, and $R_3$ can not be a hydrogen atom at the same time, and b, c and d are each an integer of 0 or 1 to 10;

(f) a polyoxyethylene glyceryl stearate represented by the formula $$\begin{array}{l} CH_2-O-R_9 \\ CH-O-(CH_2CH_2O)_eH \\ CH_2-O-(CH_2CH_2O)_fH \end{array} \quad (VI)$$

wherein $R_9$ is a stearoyl group, e and f are each an integer of 0 or 1 to 10, and e+f is an integer of 1 to 10; and (g) a propylene glycol stearate represented by the formula

$$R_9-O-CH_2\overset{CH_3}{\underset{|}{CH}}-OH \quad (VII)$$

wherein $R_9$ is as defined above.

The present inventor conducted extensive research to achieve the foregoing objects and found that when a coloring composition comprising a coloring matter, a resin and an organic solvent further contains at least one specific compound, even in a small amount, selected as a drying inhibitor from the compounds (a) to (g) as given above, the composition, even if left to stand for an extended period, would keep the solvent unevaporated and would remain substantially unchanged in the formulation, namely without impairment of properties. Since a small amount of the drying inhibitor added can remarkably inhibit drying, the addition does not adversely affect the dispersion stability of pigment, the ability to impart a good feel to a coating, etc. inherently possessed by the composition. It was also found that the hair coloring composition of the present invention held in a container of the fiber bundle wick-sucking type, even if left to stand for a prolonged period with its cap removed, would not dry nor solidify and could retain the original properties in further application, namely would allow re-use. The present invention has been accomplished based on these novel findings.

The hair coloring composition of the present invention essentially contains, as a drying inhibitor, at least one member selected from the group consisting of: (a) a glyceryl stearate of the formula (I), (b) a polyglyceryl stearate of the formula (II), (c) a sorbitan stearate of the formula (III), (d) a polyoxyethylene sorbitan stearate of the formula (IV), (e) a polyoxyethylene sorbitol stearate of the formula (V), (f) a polyoxyethylene glyceryl stearate of the formula (VI), and (g) a propylene glycol stearate of the formula (VII). The purity of these esters serving as the drying inhibitor is not critical. For example, useful drying inhibitors include those which contain not only stearic acid but palmitic acid, myristic acid and the like as the fatty acid component insofar as the content of the acids is about 50% or less.

The most preferred among the drying inhibitors (a) to (g) is the polyoxyethylene sorbitan stearate (d) of the formula (IV). This compound exhibits an activity of inhibiting drying and a dispersion stability of pigment for a longer prolonged period than the glyceryl stearate (a), polyglyceryl stearate (b), and sorbitan stearate (c). The compound (d) can be prepared by reacting a sorbitan stearate with ethylene oxide to introduce an oxyethylene group. The compound is generally obtained in the form of a mixture of: a polyoxyethylene sorbitan stearate of the formula (IV')

$$d') \; H(OCH_2CH_2)_b-O-\underset{\underset{O}{\overset{CH_2}{\diagdown}\diagup}}{CH}-\underset{CH-CHCH_2\;OR_{10}}{\overset{CH-O(CH_2CH_2O)_cH}{|}} \quad (IV')$$
$$\phantom{d') \; H(OCH_2CH_2)_b-O-CH-CH-} O-(CH_2CH_2O)_cH$$

wherein b and c are as defined above and $R_{10}$ is a stearoyl group, and a polyoxyethylene sorbitan stearate of the formula (IV'')

$$d'') \; H(OCH_2CH_2)_g-OCH-\underset{\underset{O}{\overset{CH_2}{\diagdown}\diagup}}{CH}-OR_1 \atop CHCHCH_2-OR_2 \atop OR_3 \quad (IV'')$$

wherein $R_1$, $R_2$ and $R_3$ are as defined above and g is an integer of 1 to 10.

The polyoxyethylene sorbitan stearates of the formulae (IV') and (IV''), which each have an excellent ability to inhibit drying, need not be separated from each other and can be used in mixture. Preferred among these esters are compounds of the formula (IV) wherein the number of polyoxyethylene group represented by b+2c is 2 to 9, desirably 4 to 6. That is, preferred compounds are those of the formula (IV') wherein b+2c is 2 to 9, desirably 4 to 6, and those of the formula (IV'') wherein g is 2 to 9, desirably 4 to 6.

The drying inhibitor can be used in a wide range of amount. It ranges from a minimum effective amount sufficient to inhibit drying to an amount not adversely affecting the properties of the composition. More specifically the amount of drying inhibitor used is usually about 0.05 to about 3% by weight, preferably about 0.15 to about 1% by weight, based on the composition. The amounts in the above range can effectively restrain the drying of hair coloring composition without impairment of excellent properties inherently possessed by the composition, including a rub resistance and properties of imparting a good appearance to colored hair. The drying is suppressed presumably as follows. When a hair coloring composition is exposed to air, the drying inhibitor present in the hair coloring composition is caused to form a soft, thin, stable gel layer on the surface of composition due to the interaction between the water absorbed by the inhibitor from the air and the solvent incorporated in the composition. The gel layer effectively inhibits the evaporation of solvent and retains the formulation of hair coloring composition. The drying rate of the coating applied can not be reduced because the drying inhibitor is used in a small amount.

A coloring matter (pigment), a binder resin and an organic solvent as well as the drying inhibitor are used as the components for the hair coloring composition of the present invention. Pigments, binder resins and organic solvents conventionally used as components for hair coloring preparations can be employed, as they are, in the present invention.

Coloring matters which are useful in the invention include, for example, the following which are named according to "Handbook for Coloring Matters Legally Designated" edited by Japanese Cosmetic Industry Association (published on Nov. 28, 1988).

Coloring matters designated by law

Yellow No.403 (1), No.205, No.404, No.5, No.406, No.4, No.402, No.203,
Red No.404, No.405, No.102, No.201, No.227, No.106, No.401, No.218, No.213, No.226,
Orange No.205, No.204,
Green No.401, No.3, No.201, No.202,
Black No.401,
Blue No.1, No.202, No.205, No.2, No.204, No.404,
Purple No.401, etc.

Natural coloring matters

| Color Index Number | | chemical name |
|---|---|---|
| Yellow No. | 403(1) | Disodium salt of 2,4-dinitro-1-naphthol-7-sulfonic acid |
| | 205 | 3,3-dichloro-diphenyl-4,4-bisazo-(acetoacetoanilid) |
| | 404 | 1-Phenylazo-2-naphthylamine |
| | 5 | Disodium salt of 1-p-sulfophenylazo-2-naphthol-6-sulfonic acid |
| | 406 | Monosodium salt 4-m-sulfophenylazo-diphenylamine |
| | 4 | Trisodium salt of 3-carboxy-5-hydroxy-1-p-sulfophenyl-4-p-sulfophenylazo-pyrazole |
| | 402 | Monosodium salt of 1-(4-chloro-2-sulfo-phenyl)-3-methyl-4-[p-(p-tolylsulfonoxy)phenylazo]-5-oyrazolon |
| | 203 | Disodium salt of disulfonic acid of D&C Yellow No. 11 |
| Red No. | 404 | 1-(5-nitro-2-triazo)-2-hydroxy-3-naphthoic anilide |
| | 405 | Calcium salt of 1-(3-chlor-6-sulfo-4-triazo)-2-hydroxy-3-naphthoic acid |
| | 102 | Trisodium salt of 1-(4-sulfo-1-naphthyl-azo)-2-naphthol-6,8-disulfonic acid |
| | 201 | Monosodium salt of 4(O-sulfo-p-tolylazo)-3-hydroxy-2-naphthoic acid |
| | 227 | Disodium salt of 8-amino-2-phenylazo-1-naphthol-3,6-disulfonic acid |
| | 106 | Monosodium salt of 9-(4-sulfo-2-sulfoniumphenyl)-6-diethylamino-3-(N,N-diethylimino-3-isoxanthene |
| | 401 | Disodium salt of 9-a-carboxyphenyl-6-(4-sulfo-o-toluino-3o-tolylimino)-3-isoxanthene |
| | 218 | 2,4,5,7-Tetrabromo-12,13,14,15-tetrachloro-3,6-fluorandiol |
| | 213 | 3-Ethylchloride of 9-o-carboxyphenyl-6-diethylamino-3-ethylimino-3-isoxanthene |
| | 226 | 5,5'-Dichloro-3,3'-dimethyl-thioindigo |
| Orange No. | 205 | Monosodium salt of 1-p-sulfophenylazo-2-naphthol |
| | 204 | 3,3-dichloro-diphenyl-4,4-bisazo-(1-phenyl-3-methyl-5-pyrazolone) |
| Green No. | 401 | Ferric salt of 6-sodiumsulfo-1-isonitroso-1,2-naphthoquinone |
| | 3 | Disodium salt of 4-{[4-(N-ethyl-m-sulfobenzylamino)phenyl](4-hydroxy-2-sulfoniumphenyl)methylene}-[1-(N-ethyl-N-m-sulfobenzyl)-Δ2,5-cyclohexa-dienimene] |
| | 201 | Disodium salt of 1,4-bis(o-sulfo-p-toluino)anthraquinone |
| | 202 | 1,4-Bis(p-toluino)anthraquinine |
| Black No. | 401 | Disodium salt of 8-amino-7-p-nitrophenylazo-2-phenylazo-1-naphthol-3,6-disulfonic acid |
| Blue No. | 1 | Disodium salt of 4-{[4-(N-ethyl-m-sulfobenzylamino)phenyl](2- |

| Color Index Number | | chemical name |
|---|---|---|
| | | sulfoniumphenyl)methylene}-[1-(N-ethyl-N-m-sulfobenzyl)-Δ2,5-cyclohexa-dienimine] |
| | 202 | Monosodium salt of 4-{[4-(N-ethylbenzylamino)phenyl]-(5-hydroxy-4-sulfo-2-sulfoniumphenyl)methylene}-(N-ethyl-N-benzyl)-Δ2,5-cyclohexadienimine |
| | 205 | Diammonium salt of 4-{[4-(N-ethyl-m-sulfobenzylamino)phenyl](2-sulfoiumphenyl)methylene}-[1-(N-ethyl-N-m-sulfobenzyl)-Δ2,5-cyclohexadienimine] |
| | 2 | Disodium of 5,5-indigotindisulfonic acid |
| | 204 | 3,3-Dichloroindanthrene |
| | 404 | Copper complex salt of phthalocyanine |
| Purple No. | 401 | Monosodium salt of 1-hydroxy-4-(O-sulfo-p-toluino)anthraquinone. |

β-carotene, melanin, chlorophyll, cacao dye, riboflavin, etc.

Inorganic pigments titanium oxide, black iron oxide, carbon black, red iron oxide, black titanium oxide, ultramarine, etc.

Others pyrogallol, chamomile, henna, hematin, nitroparaphenylenediamine, 1,4-diaminoanthraquinone, etc.

These coloring matters can be used singly or in mixture. The amount of the coloring matter used is not specifically limited and is widely variable, insofar as the amount corresponds to the solubility and dispersibility of the coloring matter and is suitable to achieve the desired hue and desired concentration. A preferred amount is in the range of usually about 0.3 to about 25% by weight, based on the composition.

Useful binder resins include resins commonly employed for cosmetic preparations. Examples of such resins are acrylic polymers such as an acrylic resin alkanolamine solution, acrylic acid-styrene copolymer, and acrylic acid-hydroxypropylmethacrylic acid-butyl aminoethylacrylic acid-octylamide copolymer; rosin derivatives such as rosin, rosin-modified maleic acid-based alkyd resin, and ester gum; polymethacrylic acid ester copolymers such as N-methacryloylethyl-N,N-dimethylammonium-α-methylcarboxybetaine-methacrylic acid alkyl ester copolymer; and methyl or ethyl cellulose and hydroxyalkyl cellulose derivatives. These resins can be used in the form of not only a solution but an emulsion. The amount of the binder resin used is not specifically limited and is usually in the range of about 1 to about 30% by weight, based on the composition.

Examples of useful organic solvents are ethanol, isopropanol and like lower aliphatic alcohols commonly employed for cosmetic preparations, ethyl acetate, butyl acetate and like esters, cyclohexane, toluene, xylene and like aromatic hydrocarbons, diethyl ether and like alkyl ethers, monoalkyl or dialkyl ether of glycol and like ethers, acetone, methyl ethyl ketone and like ketones, etc. The most preferred among them are lower alcohols, especially ethanol. These solvents can be used singly or in mixture. The amount of the organic solvent used is not specifically limited and in the range of about 20 to about 98% by weight, based on the composition.

When required, the hair coloring composition of the invention may further contain additives conventionally used for hair coloring preparations such as water, perfumes, acids, alkalis, viscosity modifiers, plasticizers, dispersants and the like.

The hair coloring composition of the invention can be prepared in the same manner as known processes for preparing hair coloring compositions except that the above drying inhibitor is used in the present invention along with conventional components. For example, the hair coloring composition of the invention can be prepared by fully mixing together the components with stirring at room temperature.

Containers (applicators) usable for holding the hair coloring composition commercially manufactured according to the invention are disclosed, for example, in Japanese Unexamined Utility Model Publications No.154830/1989 and No.154831/1989. A specific example of these containers will be described below with reference to the accompanying drawings, FIGS. 1 to 4.

BRIEF DESCRIPTION OF THE DRAWINGS

FIGS. 1 to 4 show an example of applicators for use in application of the present hair coloring composition to hair.

A tubular body 1 has an outer diameter enabling holding by hand, and is opened at the forward end and the rear end. The outer wall of the tubular body 1 has stepped portions 2a, 2b at its forward end region, each having stepwise diminishing diameters. The interior of the tubular body 1 is widened rearward, namely at a narrow portion 3 slightly greater in diameter than the forward end of the body 1 and at a wide portion 4 of increased diameter. A space as defined by the wide portion 4 holds therein a casing 9 containing a hair coloring composition for supply. A small clearance 11 is formed between the casing 9 and the wide portion 4. Four grooves 5a are provided for the passage of air at 4 positions on a circumference at the rear end of the narrow portion 3, the 4 positions being equidistant from each other by a distance of ¼ the circumference. The forward end of the casing 9 is supported by an abutment 6 as a boundary between the narrow portion 3 and the wide portion 4. A plug 7 is forcibly fitted into and fixed at the forward end of the narrow portion 3. Two grooves 5b axially extend for the passage of air at two symmetrically opposed positions between the plug 7 and the internal wall. A bundle of ten fibers 8 as a wick means extends through the plug 7 from its forward end to its rear end into the casing 9 to which they are attached at their rear end. The forward ends of the wick fibers 8 are projected forward, of course, from the forward end of the tubular body 1. The wick fibers 8 are able to transfer the hair coloring composition in the casing 9 to their forward ends due to the capillary action. A rear stopper 10 is forcibly fitted into and fixed at the rear end of the tubular body 1. The casing 9 is fixed so as to abut against the forward end of the rear stopper 10 and against the abutment 6 so that it is positioned as sandwiched therebetween. A groove 5c for the passage of air extends through the center of the forward end of the rear stopper 10 to provide communication between the clearance 11 and two radially opposed positions in the forward end of the rear stopper 10. A comb cap 12 is removably fitted around the first stepped portion, i.e. the stepped portion 2a, in the forward end region of the tubular body 1. Five strips 13 in the shape of comb teeth integrally extend from the forward end of the comb cap 12 on one side thereof to protrude adjacent to the forward ends of wick fibers 8 outwardly projected. The strips 13 are so arranged that their forward ends protrude from the forward ends of the wick fibers 8. A cap 14 is removably fitted around the second stepped portion, namely the stepped portion 2b, of the tubular body 1, to overspread the wick fibers 8 and the strips 13. The applicator of the above structure has the features of facilitating application and preventing the scatter of hair coloring composition.

Described above is an example of the applicator usable for application of the present hair coloring composition. Useful applicators, however, are not limited thereto and include those optionally modified in the shape of container, the numbers and arrangements of wick fibers and the comb tooth-shaped strips, etc.

Results of the Invention

The hair coloring composition of the invention would be kept from the change of formulation, namely from the deterioration of properties even by a long-term exposure to air.

Since a significantly small amount of drying inhibitor can achieve the above effect according to the invention, the composition of the invention is not impaired in the inherent excellent properties such as the dispersion stability of pigment and the ability to give a coating of good feel.

Further, when the composition of the invention is used in the above-described applicator of the fiber bundle wick-sucking type, the following results are accomplished due to the contemplated effect. Even after exposure to air in a decapped applicator for an extended period, the composition of the invention can be re-applied as well as in the first application without becoming unable to flow at the application point because a gel layer of composition is easily ruptured in re-application by its contact with a hair strand to be colored or the like. Moreover, the composition of the invention does not need knocking prior to application and can be conveniently used without wetting or scattering from the application point, hence having a commercially high value.

EXAMPLES

This invention will be described below in more detail with reference to the following examples.

Listed below are mixtures identified with trademarks and comprising a pigment, a resin and a solvent. These mixtures were used in Examples.

(1) "Yukaformer.AM-75 Black," product of Mitsubishi Petrochemical Co., Ltd.

| | |
|---|---|
| Channel Black | 10.0 wt % |
| Yukaformer.AM-75R [trademark described below in (3)] | 70.7 wt % |
| Brucine-modified anhydrous ethanol | 20.0 wt % |

(2) "Yukaformer.AM-75R," product of Mitsubishi Petrochemical Co., Ltd.

| | |
|---|---|
| Channel Black | 1.0 wt % |
| Yellow No. 205 | 3.0 wt % |
| Red No. 404 | 6.0 wt % |

-continued

| Yukaformer.AM-75R [trademark described below in (3)] | 70.7 wt % |
|---|---|
| Brucine-modified anhydrous ethanol | 20.0 wt % |

(3) "Yukaformer.AM-75R," product of Mitsubishi Petrochemical Co., Ltd.

| N-methacryloylethyl-N,N-dimethylammonium-α-N-methylcarboxybetaine-methacrylic acid alkyl ester copolymer (70000 in average molecular weight) | 30 wt % |
|---|---|
| Brucine-modified anhydrous ethanol | 70 wt % |

(4) "Plascize L-53 Black CA," product of Go-ou Chemical Industry Co., Ltd.

| Channel Black | 8.0 wt % |
|---|---|
| Plascize L-53 D.A [trademark described below in (6)] | 44.0 wt % |
| Brucine-modified anhydrous ethanol | 48.0 wt % |

(5) "Plascize L-53 Amber-A," product of Go-ou Chemical Industry Co., Ltd.

| Channel Black | 8.0 wt % |
|---|---|
| Red No. 404 | 3.0 wt % |
| Yellow No. 205 | 6.0 wt % |
| Plascize L-53 D.A [trademark described below in (6)] | 42.0 wt % |
| Brucine-modified anhydrous ethanol | 48.0 wt % |

(6) "Plascize L-53 D·A," product of Go-ou Chemical Industry Co., Ltd.

| Acrylic resin alkanolamine | 50 wt % |
|---|---|
| Brucine-modified anhydrous ethanol | 50 wt % |

Examples 1 to 21 and Comparative Examples 1 to 13

Hair coloring compositions were prepared by the following process from the components shown in Table 1 (Examples) and Table 2 (Comparative Examples) in listed amounts. The values in Tables 1 and 2 are those expressed in wt %.

Each of the drying inhibitors shown in Tables 1 and 2 was dissolved in an organic solvent. To the solution was added Yukaformer.AM-75 Black which is a mixture of a pigment, a resin and a solvent. The mixture was stirred, giving a hair coloring composition.

[Performance Test]

Figure 1:
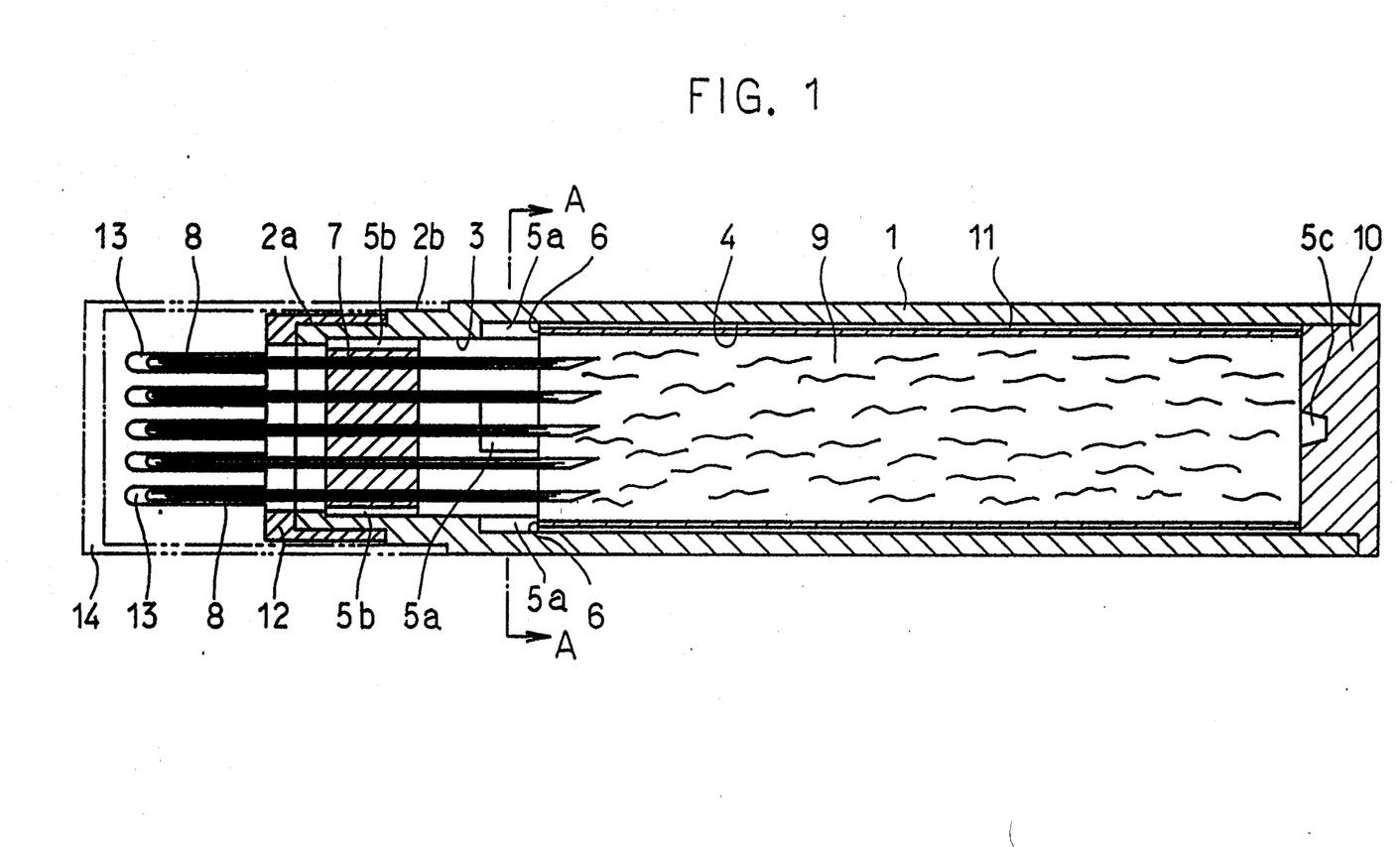
FIG. 1 is a front view showing the whole of applicator in longitudinal section.
Figure 2:
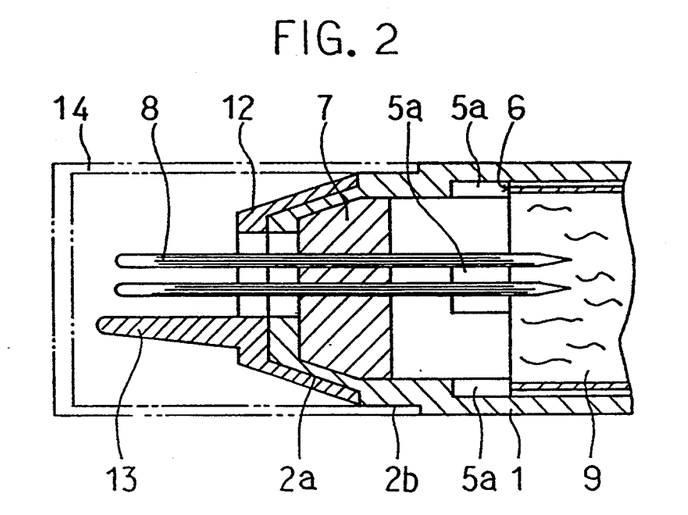
FIG. 2 is a plan view showing in longitudinal section the forward end of applicator of FIG. 1 as turned through an angle of 90°.
Figures 3, 4:
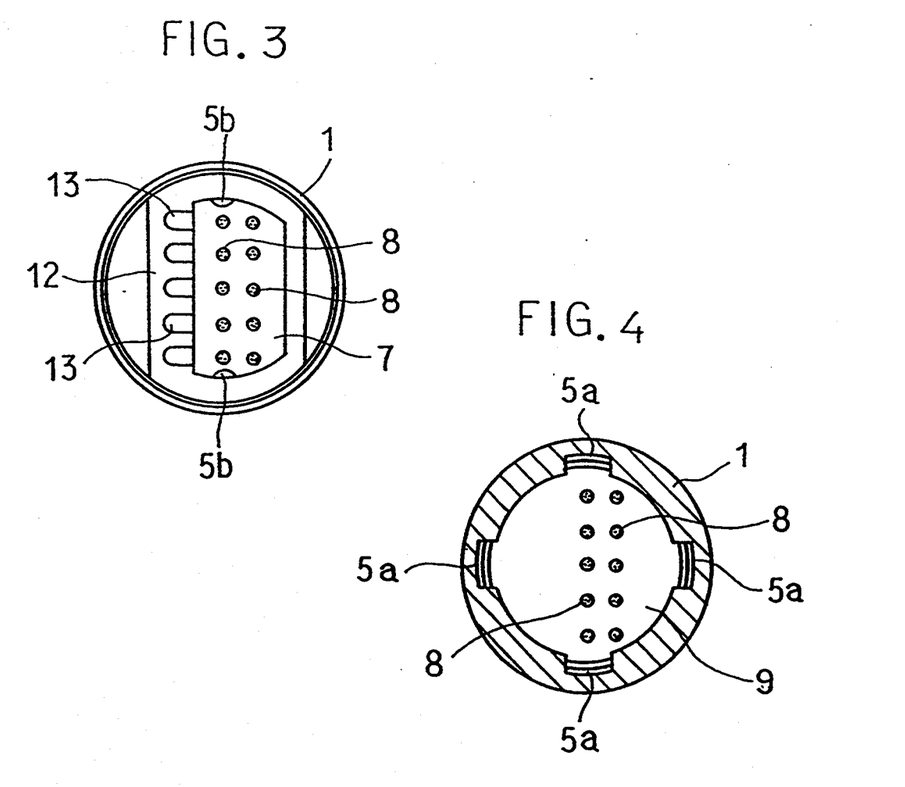
FIG. 3 is a side view showing the forward end of applicator of FIG. 1.
FIG. 4 is a sectional view taken along a line A—A of FIG. 1.

The hair coloring compositions obtained in Examples 1 to 21 and in Comparative Examples 1 to 13 were tested for the following properties using the foregoing applicator of the fiber bundle wick-sucking type as illustrated in FIG. 1 (using a reservoir). Tables 1 and 2 also show the results.

(1) Drying inhibitory property

A decapped applicator was horizontally placed and left to stand in a room (temp. 20° to 25° C., humidity 50 ±5%). Then the hair coloring composition was applied to a wool strand (2 g, 10 cm) to determine the time until which the composition was exposed to air but remained useful, namely re-applicable.

A: Re-applicable after 3 hours or longer
B: Re-applicable after 2 hours
C: Re-applicable after 1 hour
D: Not re-applicable after 1 hour (2) Appearance of colored hair The hair coloring composition was applied to 3 g of a hair strand (12 cm in length) of a healthy Japanese woman by 10 strokes of combing. In 10 minutes, the colored hair strand was checked for suppleness and degree of smooth combing. The results were evaluated according to the following criteria.

A: Supple and permitting smooth combing
B: Poor in suppleness and in degree of smooth combing
C: Not supple nor smoothly combed (3) Rub resistance The hair coloring composition was applied to 3 g of a hair strand (12 cm in length) of a healthy Japanese woman by 10 strokes of combing. In 10 minutes, the colored portion of hair strand was directly rubbed with a white cloth piece by exerting a force of about 200 g/cm$^2$. The degree of staining on the white cloth piece was evaluated according to the following criteria:

A: No stain detected on the white cloth piece
B: Slightly stained on the white cloth piece
C: Markedly stained on the white cloth piece

TABLE 1

| | | Example | | | | | |
|---|---|---|---|---|---|---|---|
| | | 1 | 2 | 3 | 4 | 5 | 6 |
| Mixture | Yukaformer.AM-75 Black | 35.0 | 35.0 | 35.0 | 35.0 | 35.0 | 35.0 |
| Solvent | Ethanol | 64.75 | 64.75 | 64.75 | 64.9 | 64.75 | 64.0 |
| Drying inhibitor | Glyceryl monostearate | 0.25 | | | | | |
| | Glyceryl distearate | | 0.25 | | | | |
| | Diglyceryl monostearate | | | 0.25 | | | |
| | Hexaglyceryl distearate | | | | 0.1 | 0.25 | 1.0 |
| | Decaglyceryl tristearate | | | | | | |
| | Decaglyceryl pentastearate | | | | | | |
| | Decaglyceryl decastearate | | | | | | |
| | Sorbitan monostearate | | | | | | |
| | Sorbitan sesquistearate* | | | | | | |
| | Sorbitan tristearate | | | | | | |
| | Polyoxyethylene (6) sorbitan monostearate** | | | | | | |
| | Polyoxyethylene (4) sorbitan monostearate | | | | | | |
| | Polyoxyethylene (3) | | | | | | |

TABLE 1-continued

|  | | | | | | |
|---|---|---|---|---|---|---|
| | sorbitan monostearate | | | | | |
| | Polyoxyethylene (2) | | | | | |
| | sorbitan monostearate | | | | | |
| | Polyoxyethylene (6) | | | | | |
| | sorbitan tristearate | | | | | |
| | Polyoxyethylene (6) | | | | | |
| | sorbitol hexastearate | | | | | |
| | Polyoxyethylene (5) | | | | | |
| | gylceryl monostearate | | | | | |
| | Polyoxyethylene (5) | | | | | |
| | glyceryl tristearate | | | | | |
| | Propylene glycol monostearate | | | | | |
| Drying inhibitory affect | | C | A | A | C | A | A |
| Appearance of colored hair | | A | A | A | A | A | A |
| Rub resistance | | A | A | A | A | A | A |

| | | Example | | | | |
|---|---|---|---|---|---|---|
| | | 7 | 8 | 9 | 10 | 11 |
| Mixture | Yukaformer.AM-75 Black | 35.0 | 35.0 | 35.0 | 35.0 | 35.0 |
| Solvent | Ethanol | 64.75 | 64.75 | 64.75 | 64.75 | 64.75 |
| Drying inhibitor | Glyceryl monostearate | | | | | |
| | Glyceryl distearate | | | | | |
| | Diglyceryl monostearate | | | | | |
| | Hexaglyceryl distearate | | | | | |
| | Decaglyceryl tristearate | 0.25 | | | | |
| | Decaglyceryl pentastearate | | 0.25 | | | |
| | Decaglyceryl decastearate | | | 0.25 | | |
| | Sorbitan monostearate | | | | 0.25 | |
| | Sorbitan sesquistearate* | | | | | 0.25 |
| | Sorbitan tristearate | | | | | |
| | Polyoxyethylene (6) sorbitan monostearate** | | | | | |
| | Polyoxyethylene (4) sorbitan monostearate | | | | | |
| | Polyoxyethylene (3) sorbitan monostearate | | | | | |
| | Polyoxyethylene (2) sorbitan monostearate | | | | | |
| | Polyoxyethylene (6) sorbitan tristearate | | | | | |
| | Polyoxyethylene (6) sorbitol hexastearate | | | | | |
| | Polyoxyethylene (5) glyceryl monostearate | | | | | |
| | Polyoxyethylene (5) glyceryl tristearate | | | | | |
| | Propylene glycol monostearate | | | | | |
| Drying inhibitory effect | | A | A | A | A | A |
| Appearance of colored hair | | A | A | A | A | A |
| Rub resistance | | A | A | A | A | A |

| | | Example | | | | |
|---|---|---|---|---|---|---|
| | | 12 | 13 | 14 | 15 | 16 |
| Mixture | Yukaformer.AM-75 Black | 35.0 | 35.0 | 35.0 | 35.0 | 35.0 |
| Solvent | Ethanol | 64.75 | 64.75 | 64.75 | 64.75 | 64.75 |
| Drying inhibitor | Glyceryl monostearate | | | | | |
| | Glyceryl distearate | | | | | |
| | Diglyceryl monostearate | | | | | |
| | Hexaglyceryl distearate | | | | | |
| | Decaglyceryl tristearate | | | | | |
| | Decaglyceryl pentastearate | | | | | |
| | Decaglyceryl decastearate | | | | | |
| | Sorbitan monostearate | | | | | |
| | Sorbitan sesquistearate* | | | | | |
| | Sorbitan tristearate | 0.25 | | | | |
| | Polyoxyethylene (6) sorbitan monostearate | | 0.25 | | | |
| | Polyoxyethylene (4) sorbitan monostearate | | | 0.25 | | |
| | Polyoxyethylene (3) sorbitan monostearate | | | | 0.25 | |
| | Polyoxyethylene (2) sorbitan monostearate | | | | | 0.25 |
| | Polyoxyethylene (6) sorbitan tristearate | | | | | |
| | Polyoxyethylene (6) sorbitol hexastearate | | | | | |
| | Polyoxyethylene (5) glyceryl monostearate | | | | | |
| | Polyoxyethylene (5) | | | | | |

TABLE 1-continued

|  |  |  |  |  |  |  |
|---|---|---|---|---|---|---|
|  | glyceryl tristearate |  |  |  |  |  |
|  | Propylene glycol monostearate |  |  |  |  |  |
| Drying inhibitory effect |  | A | A | A | A | A |
| Appearance of colored hair |  | A | A | A | A | A |
| Rub resistance |  | A | A | A | A | A |

|  |  | Example |  |  |  |  |
|---|---|---|---|---|---|---|
|  |  | 17 | 18 | 19 | 20 | 21 |
| Mixture | Yukaformer.AM-75 Black | 35.0 | 35.0 | 35.0 | 35.0 | 35.0 |
| Solvent | Ethanol | 64.75 | 64.75 | 64.75 | 64.75 | 64.75 |
| Drying inhibitor | Glyceryl monostearate |  |  |  |  |  |
|  | Glyceryl distearate |  |  |  |  |  |
|  | Diglyceryl monostearate |  |  |  |  |  |
|  | Hexaglyceryl distearate |  |  |  |  |  |
|  | Decaglyceryl tristearate |  |  |  |  |  |
|  | Decaglyceryl pentastearate |  |  |  |  |  |
|  | Decaglyceryl decastearate |  |  |  |  |  |
|  | Sorbitan monostearate |  |  |  |  |  |
|  | Sorbitan sesquistearate* |  |  |  |  |  |
|  | Sorbitan tristearate |  |  |  |  |  |
|  | Polyoxyethylene (6) sorbitan monostearate |  |  |  |  |  |
|  | Polyoxyethylene (4) sorbitan monostearate |  |  |  |  |  |
|  | Polyoxyethylene (3) sorbitan monostearate |  |  |  |  |  |
|  | Polyoxyethylene (2) sorbitan monostearate |  |  |  |  |  |
|  | Polyoxyethylene (6) sorbitan tristearate | 0.25 |  |  |  |  |
|  | Polyoxyethylene (6) sorbitol hexastearate |  | 0.25 |  |  |  |
|  | Polyoxyethylene (5) glyceryl monostearate |  |  | 0.25 |  |  |
|  | Polyoxyethylene (5) glyceryl tristearate |  |  |  | 0.25 |  |
|  | Propylene glycol monostearate |  |  |  |  | 0.25 |
| Drying inhibitory effect |  | A | A | B | B | C |
| Appearance of colored hair |  | A | A | A | A | A |
| Rub resistance |  | A | A | A | A | A |

Notes:
*A mixture of sorbitan monostearate and sorbitan distearate
**The parenthesized figure in polyoxyethylene sorbitan monostearate, e.g. (6) in polyoxyethylene sorbitan monostearate shows the number of moles of polyoxyethylene adducted, namely b + 2c in the formula IV.

TABLE 2

|  |  | Comparative Example |  |  |  |  |  |  |  |  |  |  |  |
|---|---|---|---|---|---|---|---|---|---|---|---|---|---|
|  |  | 1 | 2 | 3 | 4 | 5 | 6 | 7 | 8 | 9 | 10 | 11 | 12 |
| Mixture | Yukaformer.AM-75 Black | 35.0 | 35.0 | 35.0 | 35.0 | 35.0 | 35.0 | 35.0 | 35.0 | 35.0 | 35.0 | 35.0 | 35.0 |
| Solvent | Ethanol | 65.0 | 64.75 | 60.00 | 64.75 | 64.75 | 64.75 | 64.75 | 64.75 | 64.75 | 64.75 | 64.75 | 64.75 |
| Drying Inhibitor | Glyceryl monooleate |  | 0.25 |  |  |  |  |  |  |  |  |  |  |
|  | Diglyceryl monoisostearate |  |  | 0.25 |  |  |  |  |  |  |  |  |  |
|  | Hexaglyceryl monooleare |  |  |  | 0.25 |  |  |  |  |  |  |  |  |
|  | Sorbitan monopalmitate |  |  |  |  | 0.25 |  |  |  |  |  |  |  |
|  | Sorbitan monooleate |  |  |  |  |  | 0.25 |  |  |  |  |  |  |
|  | Sorbitan sesquioleate* |  |  |  |  |  |  | 0.25 |  |  |  |  |  |
|  | Sorbitan monoisostearate |  |  |  |  |  |  |  | 0.25 |  |  |  |  |
|  | Polyoxyethylene (20) sorbitan monostearate |  |  |  |  |  |  |  |  | 0.25 |  |  |  |
|  | Polyoxyethylene (60) sorbitan tetrastearate |  |  |  |  |  |  |  |  |  | 0.25 |  |  |
|  | Polyoxyethylene (15) glyceryl monostearate |  |  |  |  |  |  |  |  |  |  | 0.25 |  |
|  | Polyoxyethylene (5) glyceryl monooleate |  |  |  |  |  |  |  |  |  |  |  | 0.25 |
| Drying Inhibitory effect |  | D | D | D | D | D | D | D | D | D | D | D | D |
| Appearance of colored hair |  | — | — | — | — | — | — | — | — | — | — | — | — |
| Rub resistance |  | — | — | — | — | — | — | — | — | — | — | — | — |

Note: * A mixture of sorbitan monooleate and sorbitan dioleate

To determine the long-term drying inhibitory property and the long-term dispersion stability of pigment, the compositions prepared in Examples 13, 14 and 15 were tested by the following methods. Table 3 below shows the results.

(4) Long-term drying inhibitory property

The test described above in (1) was carried out to check the composition for serviceability in 48 hours. The results were evaluated according to the following criteria:

A: Serviceable
B: Not serviceable for thin spot in coating (5) Long-term dispersion stability of pigment Each test composition was charged into the applicator of the fiber bundle wick-sucking type (using a reservoir) as shown in FIG. 1. The capped applicator was placed in a thermostatic chamber at 25° C. for 1 to 3 months. After the lapse of the specified period, the chamber was opened and the liquid was sucked up from the reservoir through a syringe needle. The liquid was caused to fall in drips onto filter paper and was inspected for the change of color. The liquid permeated in the paper and having a uniform color was regarded to have the pigment well dispersed therein, whereas the liquid having a varied concentration was regarded to have the pigment dispersed therein in a deteriorated degree corresponding to the extent of variation. The dispersion stability of pigment was evaluated according to the following criteria.

A: No change
B: Slightly varied in concentration
C: Significantly varied in concentration

TABLE 3

| Ex. | Long-term drying inhibitory property | Long-term dispersion stability of pigment | | |
|---|---|---|---|---|
| | | 1 month | 2 month | 3 month |
| 13 | A | A | A | A |
| 14 | A | A | A | A |
| 15 | A | A | A | A |

Example 22

A hair coloring composition with the following formulation was prepared by the same process as in Example 1 using the same applicator as used in the performance test, and was checked for properties.

| | |
|---|---|
| "Yukaformer.AM-75 Black" (trademark) | 4.80 wt % |
| "Yukaformer.AM-75 Brown" (trademark) | 5.00 wt % |
| Orange No.205 | 0.18 wt % |
| Methylphenylpolysiloxane | 0.10 wt % |
| Polyoxyethylene (6) sorbitan monostearate | 0.30 wt % |
| Purified water | 6.00 wt % |
| Perfume (citral) | 0.02 wt % |
| Brucine-modified 95% ethanol | 83.60 wt % |

(The above composition was adjusted to a pH of 6.0 with citric acid)

The composition thus obtained was a good hair coloring composition for use in an applicator of the fiber bundle wick-sucking type which composition was able to inhibit drying for 1 hour or longer and showed no deterioration in rub resistance and in appearance of colored hair.

Example 23

A hair coloring composition with the following formulation was prepared in the same manner as in Example 22.

| | |
|---|---|
| "Yukaformer.AM-75 Brown" (trademark) | 15.00 wt % |
| Propylene glycol monostearate | 0.10 wt % |
| Sorbitan stearate | 0.20 wt % |
| Isopropanol | 5.50 wt % |
| Brucine-modified anhydrous ethanol | 79.20 wt % |

The composition thus obtained was a good hair coloring composition for use in an applicator of the fiber bundle wick-sucking type which composition was able to inhibit drying for 1 hour or longer and showed no deterioration in rub resistance and in appearance of colored hair.

Example 24

A hair coloring composition with the following formulation was prepared in the same manner as in Example 22.

| | |
|---|---|
| Plascize L-53 Amber-A (trademark) | 17.00 wt % |
| Plascize L-53 Black CA (trademark) | 3.00 wt % |
| Plascize L-53 D-A (trademark) | 2.35 wt % |
| Polyoxyethylene (6) sorbitol hexastearate | 0.20 wt % |
| Brucine-modified anhydrous ethanol | 77.45 wt % |

The composition thus obtained was a good hair coloring composition for use in an applicator of the fiber bundle wick-sucking type which composition was able to inhibit drying for 1 hour or longer and showed no deterioration in rub resistance and in appearance of colored hair.

I claim:

1. A hair coloring composition comprising about 0.3 to about 25% by weight of hair colorant selected from the group consisting of:

| Color Index Number | | chemical name |
|---|---|---|
| Yellow No. | 403(1) | Disodium salt of 2,4-dinitro-1-naphthol-7-sulfonic acid |
| | 205 | 3,3-dichloro-diphenyl-4,4-bisazo-(acetoacetoanilid) |
| | 404 | 1-Phenylazo-2-naphthylamine |
| | 5 | Disodium salt of 1-p-sulfophenylazo-2-naphthol-6-sulfonic acid |
| | 406 | Monosodium salt 4-m-sulfophenylazo-diphenylamine |
| | 4 | Trisodium salt of 3-carboxy-5-hydroxy-1-p-sulfophenyl-4-p-sulfophenylazo-pyrazole |
| | 402 | Monosodium salt of 1-(4-chloro-2-sulfo-phenyl)-3-methyl-4-[p-(p-tolylsulfonoxy)phenylazo]-5-oyrazolon |
| | 203 | Disodium salt of disulfonic acid of D&C Yellow No. 11 |
| Red No. | 404 | 1-(5-nitro-2-triazo)-2-hydroxy-3-naphthoic anilide |
| | 405 | Calcium salt of 1-(3-chlor-6-sulfo-4-triazo)-2-hydroxy-3-naphthoic acid |
| | 102 | Trisodium salt of 1-(4-sulfo-1-naphthyl-azo)-2-naphthol-6,8-disulfonic acid |
| | 201 | Monosodium salt of 4(O-sulfo-p-tolylazo)-3-hydroxy-2-naphthoic acid |
| | 227 | Disodium salt of 8-amino-2-phenylazo-1-naphthol-3,6-disulfonic acid |
| | 106 | Monosodium salt of 9-(4-sulfo-2-sulfoniumphenyl)-6-diethylamino-3-(N,N-diethylimino-3-isoxanthene |
| | 401 | Disodium salt of 9-a-carboxyphenyl-6-(4-sulfo-o-toluino-3o-tolylimino)-3-isoxanthene |
| | 218 | 2,4,5,7-Tetrabromo-12,13,14,15-tetrachloro-3,6-fluorandiol |
| | 213 | 3-Ethylchloride of 9-o-carboxyphenyl-6-diethylamino-3-ethylimino-3-isoxanthene |
| | 226 | 5,5'-Dichloro-3,3'-dimethyl-thioindigo |
| Orange No. | 205 | Monosodium salt of 1-p-sulfophenylazo-2-naphthol |

-continued

| Color Index Number | chemical name |
|---|---|
| 204 | 3,3-dichloro-diphenyl-4,4-bisazo-(1-phenyl-3-methyl-5-pyrazolone) |
| Green No. 401 | Ferric salt of 6-sodiumsulfo-1-isonitroso-1,2-naphthoquinone |
| 3 | Disodium salt of 4-{[4-(N-ethyl-m-sulfobenzylamino)phenyl](4-hydroxy-2-sulfoniumphenyl)methylene}-[1-(N-ethyl-N-m-sulfobenzyl)-Δ2,5-cyclohexadienimene] |
| 201 | Disodium salt of 1,4-bis(o-sulfo-p-toluino)anthraquinone |
| 202 | 1,4-Bis(p-toluino)anthraquinine |
| Black No. 401 | Disodium salt of 8-amino-7-p-nitrophenylazo-2-phenylazo-1-naphthol-3,6-disulfonic acid |
| Blue No. 1 | Disodium salt of 4-{[4-(N-ethyl-m-sulfobenzylamino)phenyl](2-sulfoniumphenyl)methylene}-[1-(N-ethyl-N-m-sulfobenzyl)-Δ2,5-cyclohexadienimine] |
| 202 | Monosodium salt of 4-{[4-(N-ethylbenzylamino)phenyl]-(5-hydroxy-4-sulfo-2-sulfoniumphenyl)methylene}-(N-ethyl-N-benzyl)-Δ2,5-cyclohexadienimine |
| 205 | Diammonium salt of 4-{[4-(N-ethyl-m-sulfobenzylamino)phenyl](2-sulfoiumphenyl)methylene}-[1-(N-ethyl-N-m-sulfobenzyl)-Δ2,5-cyclohexadienimine] |
| 2 | Disodium of 5,5-indigotindisulfonic acid |
| 204 | 3,3-Dichloroindanthrene |
| 404 | Copper complex salt of phthalocyanine |
| Purple No. 401 | Monosodium salt of 1-hydroxy-4-(O-sulfo-p-toluino)anthraquinone. |

β-carotene, melanin, chlorophyll, cacao dye, riboflaxin, titanium dioxide, black iron oxide, carbon black, red iron oxide, black titanium oxide, ultramarine, pyrogallol, chamomile, henna, hematin, nitroparaphenylenediamine and 1,4-diaminoanthraquinone; about 1 to about 30% by weight of a binder resin for cosmetic preparations selected from the group consisting of acrylic polymers, rosin derivatives, polymethacrylic acid ester copolymer, methyl cellulose, ethyl cellulose, and hydroxyalkyl cellulose derivatives and about 65 to about 98% by weight of lower aliphatic monohydric alcohols, characterized in that the composition further contains about 0.05 to about 3% by weight of at least one drying inhibitor selected from the group consisting of:

(a) a glyceryl stearate represented by the formula (I)

wherein $R_1$ and $R_2$ are the same or different and each represents a hydrogen atom or a stearoyl group, provided that $R_1$ and $R_2$ can not be a hydrogen atom at the same time;

(b) a polyglyceryl stearate represented by the formula (II)

wherein $R_1$, $R_2$, $R_3$, $R_4$, and $R_5$ are the same or different and each represents a hydrogen atom or a stearoyl group, provided that $R_1$, $R_2$, $R_3$, $R_4$, and $R_5$ can not be a hydrogen atom at the same time, and a is 0 or an integer of 1 to 13;

(c) a sorbitan stearate represented by the formula (III)

wherein $R_1$, $R_2$, and $R_3$ are as defined above, provided that $R_1$, $R_2$, and $R_3$ can not be a hydrogen atom at the same time;

(d) a polyoxyethylene sorbitan stearate represented by the formula (IV)

wherein $R_6$ and $R_7$ are each a stearoyl group or $-(CH_2CH_2O)_cH$, b and c are each 0 or an integer of 1 to 10, b+2c is an integer of 1 to 10, $R_8$ is a hydrogen atom or a stearoyl group, provided that when one or both of $R_6$ and $R_7$ are a stearoyl group, $R_8$ may be a hydrogen atom, but when both of $R_6$ and $R_7$ are $-(CH_2CH_2O)_cH$, $R_8$ is a stearoyl group;

(e) a polyoxyethylene sorbitol stearate represented by the formula (V)

wherein $R_1$, $R_2$, and $R_3$ are as defined above, provided that $R_1$, $R_2$, and $R_3$ can not be a hydrogen atom at the same time, and b, c and d are each 0 or an integer of 1 to 10;

(f) a polyoxyethylene glyceryl stearate represented by the formula (VI)

wherein $R_9$ is a stearoyl group, e and f are each 0 or an integer of 1 to 10 and e+f is an integer of 1 to 10; and

(g) a propylene glycol stearate represented by the formula (VII)

wherein $R_9$ is as defined above.

2. A hair coloring composition according to claim 1 wherein the drying inhibitor is the polyoxyethylene sorbitan stearate (d) of the formula (IV).

3. A composition according to claim 2 wherein the polyoxyethylene sorbitan stearate is a mixture of a polyoxyethylene sorbitan stearate represented by the formula (IV'):

d')  (IV')

wherein b and c are as defined above and $R_{10}$ is a stearoyl group, and a polyoxyethylene sorbitan stearate represented by the formula d'')

wherein $R_1$, $R_2$ and $R_3$ are as defined above, provided that $R_1$ and $R_3$ can not be a hydrogen atom at the same time, and g is an integer of 1 to 10.

4. A composition according to claim 2 wherein b+2c in the formula (IV) is 2 to 9.

5. A composition according to claim 4 wherein b+2c in the formula (IV) is 4 to 6.

6. A composition according to claim 3 wherein b+2c in the formula (IV') is 2 to 9 and g in the formula (IV'') is 2 to 9.

7. A composition according to claim 6 wherein b+2c in the formula (IV') is 4 to 6 and g in the the formula (IV'') is 4 to 6.

8. A composition according to claim 1 which contains the drying inhibitor in an amount of 0.15 to 1% by weight, based on the composition.

9. A package for coloring hair comprising a container containing the hair coloring composition of claim 1 and having a fiber bundle wick means for bringing the colorant to the outside of the container by capillary action of the fibers.

* * * * *